United States Patent

Böhm et al.

Patent Number: 5,336,809
Date of Patent: Aug. 9, 1994

[54] PROCESS FOR PREPARING 1-FLUOROCYCLOPROPYL METHYL KETONE

[75] Inventors: Stefan Böhm, Cologne; Albrecht Marhold, Leverkusen, both of Fed. Rep. of Germany

[73] Assignee: Bayer Aktiengesellschaft, Leverkusen, Fed. Rep. of Germany

[21] Appl. No.: 25,194

[22] Filed: Mar. 2, 1993

[30] Foreign Application Priority Data

Mar. 5, 1992 [DE] Fed. Rep. of Germany ....... 4206917

[51] Int. Cl.$^5$ ............................................. C07C 45/54
[52] U.S. Cl. .................................... 568/354; 549/322
[58] Field of Search ........................ 549/322; 568/354

[56] References Cited

U.S. PATENT DOCUMENTS 4,913,727  4/1990  Stroech et al. ........................ 71/92

FOREIGN PATENT DOCUMENTS 0436348 12/1990 European Pat. Off. ................. 71/92

OTHER PUBLICATIONS

Synthesis, International Journal of Methods in Synthetic Organic Chemistry, No. 3, 1977, pp. 189–191.
Tetrahedron Letters, vol. 31, No. 45, Oct. 1990, pp. 6527–6530.
Saburo Takei, Tetrahedron Letters No. 49, 1975, pp. 4389–4392.
M. B. Giudicelli, Tetrahedron Letters, vol. 31, No. 45, 1990, pp. 6527–6530.
Lutz Fitjer, Synthesis, "1,1-Bifunctional Cyclopropanes; Convenient Synthesis of 1-Bromo-, 1-Chloro-, and 1-Fluorocyclopropyl Methyl Ketone," 1977, pp. 189–191.
Chemistry Letters, 1975, p. 1152.

Primary Examiner—James H. Reamer
Attorney, Agent, or Firm—Sprung Horn Kramer & Woods

[57] ABSTRACT

A new process for the preparation of 1-fluorocyclopropyl methyl ketone of the formula

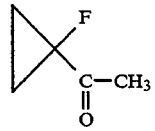

which process comprises
a) in a first step, reacting 2-acetyl-2-chloro-4-butanolide of the formula

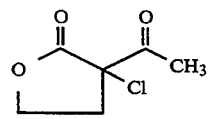

with an addition product of triethylamine and hydrogen fluoride of the formula $(C_2H_5)_3N \cdot n\ HF$ in which
n represents the numbers 1, 2 or 3,
in the presence of a diluent at a temperature between 20° C. and 120° C. and
b) in a second step, reacting the resulting 2-acetyl-2-fluoro-4-butanolide of the formula

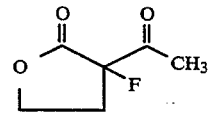

with a nucleophilic agent in the presence of a diluent at a temperature between 50° C. and 200° C.
New halogenoketones of the formula

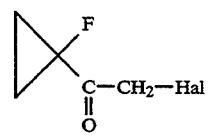

in which
Hal represents chlorine or bromine.

8 Claims, No Drawings

PROCESS FOR PREPARING 1-FLUOROCYCLOPROPYL METHYL KETONE

The present invention relates to a novel process for preparing the known 1-fluorocyclopropyl methyl ketone which can be used as an intermediate product for the synthesis of active substances having fungicidal properties.

It has already become known that 1-fluorocyclopropyl methyl ketone can be prepared by treating 2-acetyl-2-chloro-4-butanolide with potassium fluoride, by reacting the 2-acetyl-1-fluoro-4-butanolide thus produced with hydrogen bromide, and by cyclising the 5-chloro-3-fluoropentan-2-one thus formed with potassium fluoride (cf. Synthesis 1977, 189–191). This synthesis can be illustrated by the following set of equations:

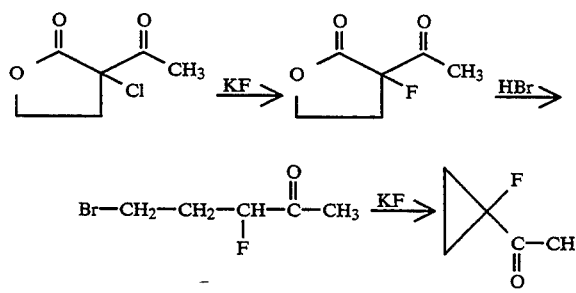

Drawbacks of the known method are that it is a three-step synthesis and that the yields for the individual reaction steps are only relatively low.

It has now been found that 1-fluorocyclopropyl methyl ketone of the formula

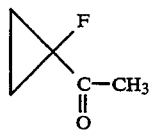  (I)

is obtained if a) in a first step, 2-acetyl-2-chloro-4-butanolide of the formula

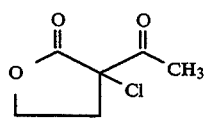  (II)

is reacted with an addition product of triethylamine and hydrogen fluoride of the formula $(C_2H_5)_3N \cdot n\ HF$  (III)

in which n represents the numbers 1, 2 or 3, in the presence of a diluent at temperatures between 20° C. and 120° C. and b) in a second step, the 2-acetyl-2-fluoro-4-butanolide of the formula

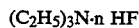  (IV)

produced is reacted with a nucleophilic agent in the presence of a diluent at temperatures between 50° C. and 200° C.

It is to be regarded as extremely surprising that 1-fluorocyclopropyl methyl ketone of the formula (I) can be prepared by the process according to the invention in a smooth reaction with a high yield. On the basis of the prior art it was to be expected, after all, that in the first step, as well as an exchange of the chlorine atom for a fluorine atom on the tertiary carbon atom, elimination reactions would also take place to a considerable extent (cf. Tetrahedron Letters 31, 6527–6530 (1990)). Also unexpected is the straightforward course of the second step, as similar reactions of substances having a halogen atom on a tertiary carbon atom had not been known until now.

The process according to the invention is notable for a number of advantages. For instance, it makes it possible to prepare 1-fluorocyclopropyl methyl ketone in very good yields and in high purity according to a method comprising one step fewer than the synthesis known hitherto. Furthermore, the starting material and the reaction components are also accessible in a simple way and in fairly large quantities, too.

If 2-acetyl-2-chloro-4-butanolide is reacted, in the first step, with the addition product of 1 mol of triethylamine and 2 mol of hydrogen fluoride, and if, in the second step, potassium iodide is used as the nucleophilic agent, the path of the method according to the invention can be illustrated by the following set of equations:

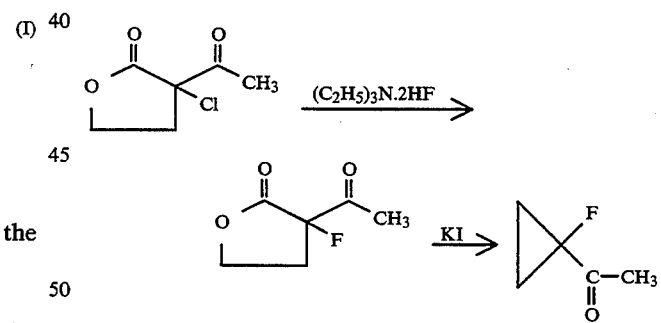

The 2-acetyl-2-chloro-4-butanolide of the formula (II), required as the starting material in carrying out the method according to the invention, is known (cf. Synthesis 1977, 189).

The addition product of triethylamine and hydrogen fluoride, required as reaction component in carrying out the process according to the invention, is characterized by the formula (III). n represents the numbers 1, 2 or 3 in this formula. Preferably, n represents the number 2.

The addition product of triethylamine and hydrogen fluoride of the formula (III), which is required as a reaction component in the first step when carrying out the method according to the invention, is also known (cf. Tetrahedron Letters 31, 6527–6530 (1990)). It is generally used in the freshly prepared state. It is prepared by adding, to a solution of the addition product from 1 mol of triethylamine and 3 mol of hydrogen fluoride in a diluent, the calculated amount of triethylamine.

Suitable nucleophilic reagents for carrying out the second step of the method according to the invention are all the substances customary for reactions of this type. Of preferred possible use are alkali metal halides, such as potassium iodide, potassium bromide, sodium iodide, sodium bromide and sodium chloride, also cyclic amines, such as 1,4-diaza-bicyclo[2,2,2]octane (DABCO), and phase transfern catalysts, such as tetramethylammonium bromide and triethyl-benzylammonium chloride.

Suitable diluents for carrying out the first step of the method according to the invention are all the organic solvents customary for reactions of this type. Of preferred possible use are aliphatic and aromatic, optionally halogenated, hydrocarbons, such as hexane, benzene, toluene and chlorobenzene, also ethers, such as tetrahydrofuran and dioxane, and, in addition, polar solvents, such as acetonitrile, dimethylformamide and N-methyl-pyrrolidone.

In carrying out the second step of the method according to the invention, suitable diluents are again all the inert organic solvents customary for reactions of this type. Of preferred possible use are high-boiling organic solvents, such as N-methyl-pyrrolidone, dimethyl sulphoxide, dimethylformamide, xylenes, hexamethylphosphoramide, 1,3-dimethylimidazolidine-2-one and so on.

The reaction temperatures may be varied within a certain range in carrying out the first step of the method according to the invention. In general, temperatures between 20° C. and 120° C., preferably between 40° C. and 100° C., are used. The first step of the method according to the invention is generally carried out under atmospheric pressure. It is, however, also possible to work under increased or reduced pressure.

In carrying out the first step of the method according to the invention, in general, 1 to 5 mol, preferably 2 to 4 mol, of the addition product of the formula (III) of triethylamine and hydrogen fluoride are used per 1 mol of 2-acetyl-2-chloro-4-butanolide of the formula (II). Conventional methods are used in working up. In general, the procedure comprises the addition of water to the reaction mixture after part of the solvent has first been distilled off, followed by extraction with an organic solvent sparingly miscible with water, washing of the combined organic phases, drying, and distillation under reduced pressure.

In carrying out the second step of the method according to the invention, too, the reaction temperatures may be varied within a certain range. In general, temperatures between 50° C. and 200° C., preferably between 100° C. and 180° C., are used.

The second step of the method according to the invention is carried out either under atmospheric pressure or under reduced pressure.

In carrying out the second step of the method according to the invention, in general 0.1 to 1 mol, preferably 0.2 to 0.8 mol, of the nucleophilic agent is used per 1 mol of 2-acetyl-2-fluoro-4-butanolide of the formula (IV). Expediently, 2-acetyl-2-fluoro-4-butanolide is added dropwise, at increased temperature and under reduced pressure, into a solution of a nucleophilic agent in an organic solvent, and the 1-fluorocyclopropyl methyl ketone generated is distilled off continuously.

To achieve further purification, the product may be subjected to another distillation.

The 1-fluorocyclopropyl methyl ketone of the formula (I) is a valuable intermediate for the synthesis of active substances having fungicidal properties (cf. EP-OS [European Patent Specification] 0,436,348 and EP-OS [European Patent Specification] 0,297,345). For example, the compound of the formula

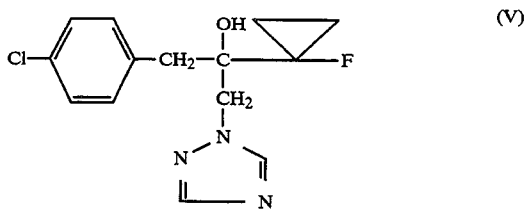

can be prepared by reacting 1-fluorocyclopropyl methyl ketone of the formula

with chlorinating or brominating agents in the presence of a diluent, by reacting the resultant halogenoketones of the formula

in which

Hal represents chlorine or bromine, with 4-chlorobenzyl-magnesium chloride of the formula

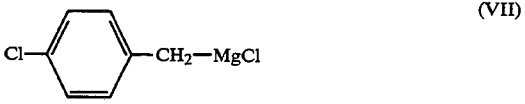

in the presence of a diluent, and by reacting the propanol derivatives thus produced of the formula

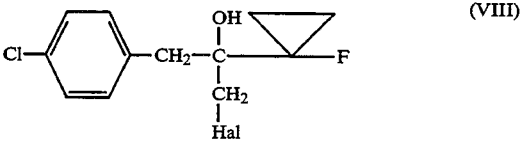

in which

Hal has the abovementioned meaning, with 1,2,4-triazole in the presence of a diluent and, if required, in the presence of an acid-binding agent.

The halogenoketones of the formula (VI) are novel. Suitable for their preparation according to the above method are all the chlorinating and brominating reagents customary for reactions of this type. By preference, sulphuryl chloride, sulphuryl bromide and bromine can be used.

Suitable diluents for preparing the halogenoketones of the formula (VI) according to the above method are all the organic solvents commonly used for reactions of this type. Of preferred possible use are halogenated aliphatic hydrocarbons, such as methylene chloride, chloroform and carbon tetrachloride.

The temperatures in the above method for the preparation of halogenoketones of the formula (VI) can be varied within a certain range. In general, temperatures between −10° C. and +60° C., preferably between 0° C. and +40° C., are used.

In carrying out the above method for the preparation of halogenoketones of the formula (VI), atmospheric pressure is generally used. It is also possible, however, to work under increased or reduced pressure.

In carrying out the above method for the preparation of halogenoketones of the formula (VI), in general, a stoichiometric amount or, alternatively, an excess of chlorinating or brominating agent is used per 1 mol of 1-fluorocyclopropyl methyl ketone of the formula (I). Conventional methods are used in working up. In general, the procedure comprises the addition of water to the reaction mixture, separation of the phases, and washing, drying, and concentration of the organic phases. The remaining residue is subjected to distillation under reduced pressure.

The implementation of the process according to the invention is illustrated by the following examples.

PREPARATION EXAMPLE

EXAMPLE 1

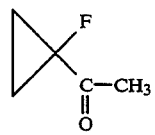
(I)

a) Preparation of 2-acetyl-2-fluoro-4-butanolide of the formula

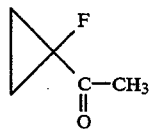
(IV)

162.6 g (1 mol) of 2-acetyl-2-chloro-4-butanolide are dissolved in 500 ml of acetonitrile, followed by the addition, with the exclusion of moisture, of 340 g (2 mol) of an addition product from 1 mol of triethylamine and 3 mol of hydrogen fluoride. 100 g (1 mol) of triethylamine are then added, and the reaction mixture is heated at 80° C. for 3 hours under stirring. Subsequently, approximately 400 ml of solvent are distilled off, and the residue is poured onto water. The resulting mixture is extracted with dichloromethane. The combined organic phases are washed with saturated aqueous sodium hydrogen-carbonate solution, dried over magnesium sulphate and concentrated under reduced pressure. By fractional distillation of the remaining residue under reduced pressure, 95 g (65% of theory) of 2-acetyl-2-fluoro-4-butanolide are obtained in the form of a colourless oil which boils at 65° C. under a pressure of 0.15 mbar.

b) Preparation of 1-fluorocyclopropyl methyl ketone of the formula

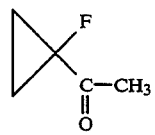
(I)

To a mixture of 16 g (0.1 mol) of potassium iodide in 80 ml of absolute N-methylpyrrolidone, 36.5 g (0.25 mol) of 2-acetyl-2-fluoro-4-butanolide are added dropwise at 180° C. under a pressure of 500 mbar. By distilling off continuously, 14 g of a product which, according to the gas chromatogram, still contains approximately 20% of N-methyl-pyrrolidone are obtained. The product is subjected to fractional distillation under atmospheric pressure. In this way, 11.2 g (44% of theory) of 1-fluorocyclopropyl methyl ketone of boiling point 88° to 90° C. are obtained.

Application Example

Preparation of the compound of the formula

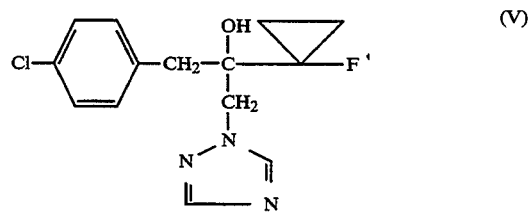
(V)

a) Preparation of 1-fluorocyclopropyl chloromethyl ketone of the formula

(VI-1)

With exclusion of moisture, 67.5 g (0.5 mol) of sulphuryl chloride are added at room temperature while stirring to a mixture of 40 g (0.4 mol) of 1-fluorocyclopropyl methyl ketone and 100 ml of methylene chloride. After the addition is completed, the mixture is stirred for 6 hours more at room temperature. The reaction mixture is then poured onto ice water, the phases are separated, the organic phase is washed with water and dried over calcium chloride, and the solvent is stripped off under reduced pressure. The remaining residue is distilled under reduced pressure. In this way, 31.8 g (58% of theory) of 1-fluorocyclopropyl chloromethyl ketone are obtained in the form of a colourless oil.

B.p.=50° C./22 mbar.

$^1$H-NMR (200 MHz, CDCl$_3$, TMS-intern.):

δ=1.46 ppm (s, 2H); 1.53 ppm (m,2H), 4.65 ppm (d, 2H).

$^{19}$F-NMR (200 MHz, CDCl$_3$, CFCl$_3$): δ=201.7 ppm (m).

b) Preparation of 1-chloro-2-(1-fluorocyclopropyl)-3-(4-chlorophenyl)-propan-2-ol of the formula

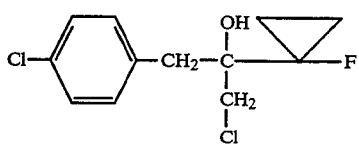 (VIII-1)

A solution of 37.3 g (0.25 mol) of 4-chloro-benzyl chloride in 400 ml of absolute diethyl ether is added dropwise at room temperature to a mixture of 6.8 g (0.28 mol) of magnesium turnings and 150 ml of absolute diethyl ether. The mixture is heated for 30 minutes under reflux, and the solution thus produced is then added dropwise at −78° C. while stirring to a solution of 34.1 g (0.25 mol) of 1-fluorocyclopropyl chloromethyl ketone in 250 ml of absolute diethyl ether. The reaction mixture is stirred for 4 hours at −78° C. It is then allowed to warm slowly to 0° C., and then a solution of 25 ml of acetic acid in 250 ml of diethyl ether is added dropwise. The reaction mixture produced is poured into 1000 ml of water. The organic phase is separated, washed with aqueous sodium hydrogen sulphite solution and with water, dried over sodium sulphate and concentrated under reduced pressure. In this way, 48.7 g (74% of theory) of 1-chloro-2-(1-fluorocyclopropyl)-3-(4-chlorophenyl)-propan-2-ol are obtained in the form of an oily product.

c) Preparation of 1-(4-chlorophenyl)-2-(1-fluorocyclopropyl)-3-(1,2,4-triazol-1-yl)-propan-2-ol of the formula

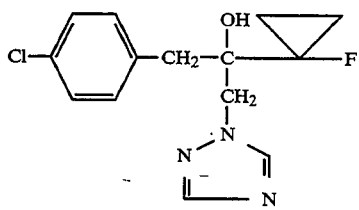 (V)

Under an atmosphere of nitrogen, 27.6 g (0.4 mol) of 1,2,4-triazole and 33.6 g (0.3 mol) of potassium tert.-butylate in 100 ml of absolute dimethylformamide are introduced as an initial charge and heated to 80° C. At this temperature, a solution of 26.3 g (0.1 mol) of 1-chloro-2-(1-fluoro-cyclopropyl)-3-(4-chlorophenyl)-propan-2-ol in 50 ml of absolute dimethylformamide is added dropwise thereto while stirring. The mixture is stirred for another 6 hours at 100° C. and then concentrated by stripping off the diluent under reduced pressure. The residue is taken up in ethyl acetate, the solution is washed with water, and, after drying over sodium sulphate, the solvent is evaporated under reduced pressure. The product left behind is chromatographed on a silica gel column, using chloroform as the mobile solvent. In this way, 8.9 g (35% of theory) of 1-(4-chlorophenyl)-2-(1-fluoro-cyclopropyl)-3-(1,2,4-triazol-1-yl)-propan-2-ol are obtained in the form of a solid.

Comparison Example

Preparation of 1-fluorocyclopropyl methyl ketone following the method according to Synthesis 1977, 189–191:

a) Preparation of 2-acetyl-2-fluoro-4-butanolide of the formula

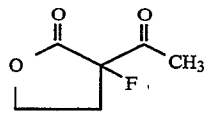 (IV)

To a solution of 162.5 g (1 mol) of 2-acetyl-2-chloro-4-butanolide in 700 ml of acetonitrile, 174.3 g (3 mol) of potassium fluoride and 0.1 g of 18-crown-6 are added. The reaction mixture is first heated under reflux for 104 hours and then concentrated by distilling off a large portion of the solvent under atmospheric pressure. The remaining residue is distilled to dryness under reduced pressure. The distillate collected is distilled once more under reduced pressure on an 80 cm long Vigreux column. In this way, 37.4 g (26% of theory) of 2-acetyl-2-fluoro-4-butanolide are obtained.

b) Preparation of 5-bromo-3-fluoro-pentan-2-one of the formula

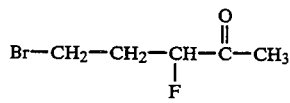

To 73 g (0.5 mol) of 2-acetyl-2-fluoro-4-butanolide, 280 ml of 48% strength hydrobromic acid are added, and the mixture is stirred at 60° C. for 3 hours. The mixture is then poured into 400 ml of water, and extracted twice with 200 ml portions of diethyl ether. The combined organic phases are washed successively with saturated aqueous sodium hydrogen-carbonate solution and with saturated aqueous sodium chloride solution. After drying over molecular sieve, the organic phase is concentrated by stripping off the solvent under reduced pressure. The remaining residue is distilled under reduced pressure. In this way, 45.6 g (50% of theory) of 5-bromo-3-fluoro-pentan-2-one are obtained.

c) Preparation of 1-fluorocyclopropyl methyl ketone of the formula

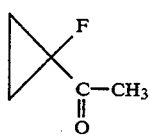 (I)

into a two-necked flask equipped with magnetic stirrer, dropping funnel and short-path distillation head, 11.6 g (0.2 mol) of potassium fluoride and 40 ml of diethylene glycol are introduced as the initial charge. At 110° C. and 90 mbar, 18.3 g (0.1 mol) of 5-bromo-3-fluoro-2-pentanone are then added dropwise, causing the product to distil off continuously. After 30 minutes, the pressure is reduced to 15 mbar for 15 minutes. The distillate is dried over magnesium sulphate and distilled on an annular-gap column. In this way, 4.1 g (40% of theory) of 1-fluorocyclopropyl methyl ketone are obtained.

It will be understood that the specification and examples are illustrative but not limitative of the present invention and that other embodiments within the spirit and scope of the invention will suggest themselves to those skilled in the art.

What is claimed is:

1. A process for the preparation of 1-fluoro-cyclopropyl methyl ketone of the formula

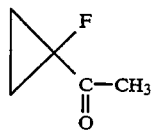

which process comprises a) in a first step, reacting 2-acetyl-2-chloro-4-butanolide of the formula

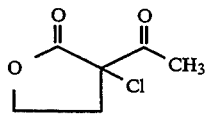

with an addition product of triethylamine and hydrogen fluoride of the formula (C$_2$H$_5$)$_3$N·n HF in which n represents the numbers 1, 2 or 3, in the presence of a diluent at a temperature between 20° C. and 120° C. and b) in a second step, reacting the resulting 2-acetyl-2-fluoro-4-butanolide of the formula

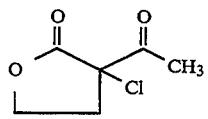

with a nucleophilic agent selected from the group consisting of an alkalimetal halide, a cylic amine, tetramethylammonium bromide and triethyl-benzyl-ammonium chloride, in the presence of a diluent at a temperature between 50° C. and 200° C.

2. A process as claimed in claim 1, wherein the addition product of 1 mol of triethylamine and 2 mol of hydrogen fluoride is used as a reaction component.

3. A process as claimed in claim 1, wherein the first step is carried out in the presence of a diluent selected from an optionally halogenated aliphatic hydrocarbon, an optionally halogenated aromatic hydrocarbon, an ether and a polar solvent.

4. A process as claimed in claim 1, wherein the diluent in the second step is a high-boiling organic solvent.

5. A process as claimed in claim 1, wherein the first step is carried out at a temperature between 40° C. and 100° C.

6. A process as claimed in claim 1, wherein the second step is carried out at a temperature between 100° C. and 180° C.

7. A process as claimed in claim 1, wherein the first step is carried out in the presence of 1 to 5 mol of an addition product of triethylamine and hydrogen fluoride per 1 mol of 2-acetyl-2-chloro-4-butanolide.

8. A process as claimed in claim 1, wherein the second step is carried out in the presence of 0.1 to 1 mol of a nucleophilic agent per 1 mol of 2-acetyl-2-fluoro-4-butanolide.

* * * * *

UNITED STATES PATENT AND TRADEMARK OFFICE
CERTIFICATE OF CORRECTION

PATENT NO. : 5,336,809
DATED : August 9, 1994
INVENTOR(S) : Bohm, et al.

It is certified that error appears in the above-identified patent and that said Letters Patent is hereby corrected as shown below:

Col. 10, line 5,   delete the structure

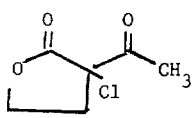

and substitute

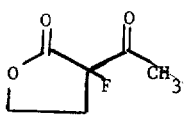

Signed and Sealed this

Twelfth Day of January, 1999

Attest:

Attesting Officer    Acting Commissioner of Patents and Trademarks